(12) United States Patent
Shibuya et al.

(10) Patent No.: US 6,224,872 B1
(45) Date of Patent: May 1, 2001

(54) COMPOSITION

(75) Inventors: Takashi Shibuya; Takeshi Ario; Shigeharu Fukuda, all of Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/118,897

(22) Filed: Jul. 20, 1998

(30) Foreign Application Priority Data

Jul. 31, 1997 (JP) .................................................. 9-218916

(51) Int. Cl.[7] .................................................. A61K 35/78
(52) U.S. Cl. ........................ 424/195.1; 514/25; 514/233.5
(58) Field of Search ...................... 424/195.1; 514/233.5, 514/25

(56) References Cited

U.S. PATENT DOCUMENTS

| 5,026,833 | 6/1991 | Suzuki et al. . |
| 5,627,157 | 5/1997 | Hijiya et al. . |

FOREIGN PATENT DOCUMENTS

| 0455432 | 4/1991 | (EP) . |
| 2258865 | 2/1993 | (GB) . |
| 37593 | 1/1991 | (JP) . |
| 3115292 | 5/1991 | (JP) . |
| 413691 | 1/1992 | (JP) . |
| 4312597 | 4/1992 | (JP) . |
| 532690 | 2/1993 | (JP) . |

OTHER PUBLICATIONS

The Japanese Pharmacopoeia, 13th Edition, p. 34 (1996).
The Japanese Pharmacopoeia, 13th Edition, p. 51–55 (1996).
Zoku–Iyakuhin–no–Kaihatsu (Development of Pharmaceuticals, second series) "Animal Models for Diseases," edited by Hideomi Fukuda et al., vol. 2 pp. 95–96 (1993).
Folia Pharmacol. Jpn. vol 104, pp. 39–49 (1994).
Katayama, S., et al., "A New Method for Extraction of Extravasated Dye in the Skin and the Influence of Fasting Stress on Passive Cutaneous Anaphylaxis in Guinea Pigs and Rats," *Microbiol. Immunol* 22–2:89–101 (1978).
Nishimoto N., et al., "Ecdysteroids from Pfaffia Iresinoides and Reassignment of Some CNMR Chemical Shifts," Phytochemistry 26–9:2505–2507 (1987).
Shiobara, Y., et al., "A Nortriterpenoid, Triterpenoids and Ecdysteroids from Pfaffia Glomerata," Phytochemistry 32–6:1527–1530 (1993).
Enzyme Handbook, published by Asakura–Shoten Publisher, Tokyo Japan (1982).
Illustrated Cyclopedia of Brazilian Medicinal Plants, pp. 24–27.

*Primary Examiner*—Leon B. Lankford, Jr.
(74) *Attorney, Agent, or Firm*—Browdy and Neimark

(57) ABSTRACT

A composition which comprises a flavonoid and a processed product of a plant of the genus Pfaffia. The composition effectively maintains and promotes the health, treats and prevents diseases, and exerts immunoenhancement, antiallergic, psychotropic, and/or tonic activities.

20 Claims, No Drawings

COMPOSITION

BACKGROUND OF THE INVENTION

1. Field of the Invention

The present invention relates to a novel composition, and more particularly, to a novel composition comprising a flavonoid and a processed product of a plant of the genus Pfaffia (may be abbreviated as processed Pfaffia product, hereinafter).

2. Description of the Prior Art

Most of the human diseases have become to be relatively-easily cured as the outstanding progress of Western medicine. The treatment of Western medicine, however, may not always sufficiently attain their prescribed effects because they, in some cases, may cause negative results and induce serious side effects. As the increase of recent health consciousness, it is highly required to establish compositions that are effective in the maintenance/promotion of health and in the treatment/prevention of human diseases without serious side effects even if used successively. For such purposes, folk medicines, which are conventionally used for a long time by humans, have become to be refocussed, but they have a demerit of insufficient therapeutic effect.

Isolating effective ingredients from folk medicines and removing ingredients other than the effective ingredients can be considered as an effective means to overcome the above demerit. However, in fact, the therapeutic effect of folk medicines would not generally be exerted with only a specific ingredient, and in most cases, desired therapeutic effect may not be exerted even if a desired effective ingredient was once isolated.

SUMMARY OF THE INVENTION

The present inventors focused on folk medicines which have been used anciently and on habitually-eaten-plants all over the world, and screened for compositions to solve the above object, from the natural world. As a result, they found that plants of the genus Pfaffia, which naturally grow in South America and have been used anciently as folk medicines, exert stronger immunoenhancement and anti-allergic activities than other folk medicines in general when prepared into a composition together with flavonoids. Since the composition has an extremely-lower toxicity and a reduced astringency and harshness inherent to Pfaffia, it can be easily administered orally and used in the maintenance/promotion of health and in the treatment/prevention of diseases. Thus the present inventors accomplished this invention.

DETAILED DESCRIPTION OF THE INVENTION

The composition according to the present invention contains a flavonoid and a processed product of a plant of the genus Pfaffia (may be designated as "Pfaffia", hereinafter). The processed product used in the present invention includes processed products in general which can be obtained by physically and/or chemically treating plants of the genus Pfaffia, and the materials and processes thereof are not specifically restricted. Examples of the plants of the genus Pfaffia are those of the species *Pfaffia glomerata, Pfaffia iresinoides, Pfaffia jubata, Pfaffia paniculata, Pfaffia pulverulenta*, and *Pfaffia spicata*. The processing of physical and/or chemical treatments used in the present invention includes minced, disrupted, ground, pulverized, pressed, fermented and/or extracted products of the plants. The processed products generally contain ecdysterone and/or its derivatives such as rubrosterone and pterosterone.

Explaining the process for producing the processed products according to the present invention, the starting materials therefore include one or more plants selected from the aforesaid plants of the genus Pfaffia and their mutants which are obtainable by conventional breeding of the plants. These plants include naturally and artificially growing plants or cultures of tissue cultures, callus cultures, cell cultures, etc. In the case of using plant bodies as the starting materials, the followings can be used arbitrarily; the whole plant bodies, or one or more specific organs selected from roots, stems, leaves, corollas, petals, pollens, stamens, pistils, seeds, albumens, and fibrils, which are partially separated from of the plant bodies. The materials can be used independently of their forms such as fresh, moisture, and dried forms. Particularly, dried roots of *Pfaffia glomerata* can be advantageously used in the present invention.

The processed Pfaffia product used in the present invention can be obtained by subjecting to the above starting materials physical and/or chemical treatments used in general in the food and pharmaceutical industries; Conventional treatments such as mincing, disruption, grounding, pulverizing, pressing, fermenting, and extracting alone or in an appropriate combination with other techniques such as filtration, concentration, and drying can produce minced, disrupted, ground, pulverized, pressed, fermented and extracted products used as the present processed products.

Explaining in more detail the process for producing Pfaffia extracts used as the processed products of Pfaffia in the present invention, it comprises the steps of treating the starting materials with appropriate treatments of mincing, disruption, pulverization, etc., and treating the resulting mixtures with conventional extraction methods using appropriate solvents. Water, other aqueous organic solvents, and water-insoluble organic solvents can be preferably used as solvents for extraction, and in particular the use of water, aqueous organic solvents, and their aqueous systems facilitates the present process. Examples of the aqueous organic solvents are ethanol, methanol, propanol, 2-propanol, acetone, etc. When used as extracting solvents, the organic solvents in 50 v/v % or lower of their aqueous systems can be used in the present invention. The extracting solvents can be arbitrarily adjusted to a desired pH level by using appropriate buffers, etc. The extracting solvents thus obtained are added to the starting materials in an appropriate amount, usually in an amount of 0.1–30-folds by weight, and if necessary, the materials are treated by stirring and heating methods for extraction. The resulting extracts are then separated into liquid and residual parts by appropriate methods such as filtration, centrifugation, and decantation, followed by collecting the liquid part as the Pfaffia extract used in the present invention. With repeated similar extraction treatment for the residual part, the resulting liquid parts can be freely pooled into the present extract. In the case of applying at least twice extractions to the starting materials and residues, different extraction solvents can be used in each extraction, followed by collecting the desired liquid parts only or pooling them into the Pfaffia extract used in the present invention.

These extracts thus obtained can be arbitrarily used as processed Pfaffia products through appropriate purification treatments. The extract usually contains secondary metabolites such as alkaloids, terpenoids, steroids, phenols, and pigments, as well as saccharides, proteins, amino acids, nucleotides, peptides, and lipids. One or more of these ingredients can be purified by applying purification methods generally used in this field. Depending on the types of the ingredients, an appropriate method can be chosen, for example, from filtration, concentration, centrifugation, crystallization, separation using solvents, separatory sedimentation, dialysis, hydrophobic chromatography, reverse-phase chromatography, adsorption chromatography, affinity chromatography, gel filtration chromatography, and/or ion-exchange chromatography.

The processed Pfaffia product thus obtained can be arbitrarily used intact in the invention, and can be further concentrated and dried or admixed with the later described physiologically-acceptable appropriate ingredients into liquids, solids, powders, pastes, semi-solids, emulsions, suspensions, etc. In the concentration and drying, conventional methods generally used in the food and pharmaceutical industries can be arbitrarily used; concentration in vacuo, membrane filtration, reverse-osmosis membrane concentration, ultrafiltration membrane filtration, drying in vacuo, freeze-drying, and spray-drying.

As described above, the processed Pfaffia product used in the present invention usually contains 0.1–10 w/w % ecdysterone, on a dry solid basis (d.s.b.), and may contain derivatives of ecdysterone such as rubrosterone and pterosterone. The ecdysterone and its derivatives contained in the processed Pfaffia product can be detected, for example, by high-performance liquid chromatography (abbreviated as "HPLC" hereinafter) for reverse phase chromatography. The solid content of the product can be determined by calculating the water content obtained in the drying reduction test as described in *The Japanese Pharmacopoeia*, 13th Edition, page 34 (1996), and the Karl Fisher method described in *The Japanese Pharmacopoeia*, 13th Edition pp. 51–55 (1996), published by Daiichi-Hoki Publishing Ltd., Tokyo, Japan.

The flavonoids used in the invention include flavonoids in general; flavanones such as hesperetin, naringenin, eriodictyol, citronetin, hesperidin, naringin, eriodictin, and citronin; flavonols such as quercetin, myricetin, rutin, and myricitrin; flavones such as baicalein, apigenin, baicalin, and apiin; and isoflavones such as genistein and genistin. Furthermore, the flavonoids include their enzyme-treated products obtained by the action of hydrolytic enzymes and saccharide-transferring enzymes. These flavonoids can be used independently of their origins and sources. For example, any of those from natural sources such as citrus plants and those obtainable by chemical synthesis can be used.

In the present invention the aforesaid flavonoids can be arbitrarily used, and particularly other flavonoids known as vitamin P such as hesperidin, rutin, naringin, eriodictin, hesperetin, quercetin, naringenin, and eriodictyol, as well as enzyme-treated hesperidin, naringin, and eriodictin, can be arbitrarily used. Among the enzyme-treated flavonoids, those obtainable by the action of saccharide-transferring enzymes are generally produced either by transferring monosaccharides including glucose, fructose, and galactose to intact flavonoids or transferring oligo- or poly-saccharides consisting of one or more of the monosaccharides to intact flavonoids. The enzyme-treated flavonoids thus obtained can be advantageously used in the present invention because they have satisfactory properties inherent to flavonoids, increased water-solubility than that of intact flavonoids, and improved light-tolerance.

The process for producing the enzyme-treated products is not specifically restricted; the products can be prepared by the action of enzymes such as cyclomaltodextrin glucanotransferase, α-glucosidase, β-glucosidase, β-fructofuranosidase, and β-galactosidase. Depending on the enzymes used, the enzyme-treated products can be prepared by mixing one or more of the above flavonoids and one or more of appropriate saccharides in appropriate solvent systems such as water and aqueous organic solvent systems, optionally adjusting the mixtures to a desired pH, adding any one of the above enzymes, and incubating the mixtures at an appropriate temperature for enzymatic reaction. The type of saccharides, pHs, and temperatures used in the enzymatic reaction are set depending on the properties of enzymes used, i.e., substrate specificity, optimum pH, pH stability, optimum temperature, thermal stability, etc. The properties of the enzymes are described, for example, in "Enzyme Handbook", published by Asakura-Shoten Publisher, Tokyo, Japan (1982). Japanese Patent Kokai Nos. 7,593/91, 115,292/91, 13,691/92, 312,597/92, and 32,690/93 applied by the present applicant disclose in detail the process for producing the enzyme-treated products using cyclomaltodextrin glucanotransferase. Commercially available products such as enzyme-treated rutin or hesperidin, alias saccharide-transferred hesperidin or saccharide-transferred vitamin P, can be arbitrarily used in the present invention as the enzyme-treated products.

The composition according to the present invention may include processed products of plants that contain caffeine and/or indican. The processed products of caffeine-containing plants include processed products in general obtained by physical and/or chemical treatments for plants that contain caffeine in the bodies or intracellularly, and their origins and production methods are not specifically restricted. Plants of the genera Paullinia, Coffea, *Thea sinensis* and Cola can be mentioned as the caffeine-containing plants. The processed products thereof generally contain caffeine and/or its derivatives. The processed products of indican-containing plants include processed products in general obtained by physical and/or chemical treatments for plants that contain indican in the bodies or intracellularly, and their origins and production methods are not specifically restricted. Plants of the genera Percicaria and Indigofera can be mentioned as the indican-containing plants. The processed products thereof may contain indican and/or its derivatives.

Explaining the caffeine- and indican-containing plants used in the present invention and the processes for producing their processed products, one or more of the above plants and their mutants obtainable by raising in conventional manner can be exemplified as the material plants. The plants may be native plants and cultured plants or cultures obtainable by tissue-, callus-, and cell-cultures. In the case of using plant bodies as the starting materials, the followings can be used freely; any of the whole plant bodies and one or more of specific organs, which are partially separated from the plant bodies, such as roots, stems, leaves, corollas, petals, pollens, stamens, pistils, seeds, albumens, and fibrils. The starting materials in fresh conditions, i.e., in a moisture form, or in a dried form can be used. In particular, dried seeds of Guarana, a plant of the genus Paullinia, can be advantageously used as a caffeine-containing plant, and fresh leaves and/or stems of an indigo plant, a plant of the genus Percicaria, (may be abbreviated as "indigo" hereinafter) can be advantageously used as an indican-containing plant.

The processed products of caffeine- and/or indican-containing plants used in the present invention can be obtained by subjecting physical and/or chemical treatments generally used in the food and pharmaceutical industries to the above starting materials. For example, the processed products in the form of minced, disrupted, ground, pulverized, pressed, fermented, and extracted products can be obtained by appropriate combination of conventional treatments such as mincing, disrupting, grinding, pulverizing, pressing, fermenting, and extracting; and other treatments such as filtering, concentrating, and drying.

Explaining in more detail the process for producing the plant extracts as the processed products of caffeine- and/or indican-containing plants used in the present invention, the starting materials are generally first subjected to appropriate treatments such as mincing, grinding, and disrupting, then subjected to conventional extractions using appropriate solvents. Water, aqueous organic solvents other than water, and water-insoluble organic solvents can be arbitrarily used as the extraction solvents, and particularly the use of water, aqueous organic solvents, and aqueous systems of the organic solvents can be advantageously practiced in the present invention. The aqueous organic solvents include, for example, ethanol, methanol, propanol, 2-propanol, and acetone. In the case of using aqueous solutions of the organic solvents as the extraction solvents, 70% or lower by volume of aqueous solvents thereof can be arbitrarily used in the present invention independently of the concentration of the organic solvents. The extraction solvents can be arbitrarily adjusted to a desired pH level using appropriate buffers, etc. The aforesaid extraction solvents are added to the starting materials in an appropriate amount, usually in an amount of 0.1–50-folds by weight, and if necessary they are subjected to stirring and heating treatments for extraction. Using appropriate methods such as filtration, centrifugation, and decantation, the extracts thus obtained can be separated into liquid and/or residual parts, followed by collecting the liquid parts as the caffeine- and/or indican-containing plant extracts used in the present invention. The residual parts can be arbitrarily subjected to a similar extraction treatment repeatedly, followed by pooling the collected liquid parts into a desired extract. When the starting materials and residues are extracted twice, they can be extracted with different extraction solvents for collecting the desired liquid parts only, and optionally, the liquid parts can be pooled into the extract usable in the present invention.

The extracts so obtained can be further treated with appropriate purification treatments into processed products of caffeine- and/or indican-containing plants before use. Generally, these extracts contain secondary metabolites such as alkaloids, terpenoids, steroids, phenols, and pigments, as well as saccharides, proteins, amino acids, nucleotides, peptides, and lipids. One or more appropriate ingredients contained in the above compounds can be purified by conventional purification methods used in this field. Depending on the type of the desired ingredient, the purification method therefor can be appropriately selected from filtration, concentration, centrifugation, crystallization, separation using solvents, separatory sedimentation, dialysis, hydrophobic chromatography, reverse-phase chromatography, adsorption chromatography, affinity chromatography, gel filtration chromatography, and/or ion-exchange chromatography.

The processed products containing caffeine- and/or indican-containing plants thus obtained can be arbitrarily used intact, and if necessary they can be further concentrated and dried, or freely admixed with the later described physiologically-acceptable appropriate ingredients into desired shapes in the from of liquids, solids, powders, pastes, semi-solids, suspensions, etc. As the methods for concentrating and drying, conventional methods used in the food and pharmaceutical industries such as concentration in vacuo, concentration using membrane filters, concentration using reverse osmosis membranes, ultrafiltration concentration, drying in vacuo, freeze drying, spray drying, etc., can be arbitrarily used.

As described above, the processed products of caffeine-containing plants used in the present invention usually contain 0.1–20 w/w % caffeine and/or its derivatives, d.s.b. The caffeine and/or its derivatives can be detected, for example, by HPLC for reverse-phase chromatography. The solid content of the processed products can be determined by calculating the moisture content using the drying reduction test or the Karl Fisher method described in *The Japanese Pharmacopoeia*, 13th Edition pp.51–55 (1996), published by Daiichi-Hoki Publishing Ltd., Tokyo, Japan.

The composition according to the present invention can be obtained by mixing the above processed Pfaffia products and flavonoids, and optionally by mixing one or more ingredients selected from the above processed products of caffeine- and/or indican-containing plants. The mixing method for such purposes is not specifically restricted and any technique used in the food and pharmaceutical industries can be advantageously used. Although the proportion of the ingredients is not specifically restricted, flavonoids are preferably added to the processed Pfaffia products in an amount of 0.001–1-fold by weight of the processed Pfaffia products, d.s.b., to effectively exert all of the later described properties of the present composition. When the processed products of caffeine- and indican-containing plants are further incorporated into the composition, they can be substantially-freely mixed independently of specific proportion, and preferably they can be respectively mixed with the processed Pfaffia products in an amount of 0.01–10-folds and 0.0001–0.1-fold by weight of the processed Pfaffia products, d.s.b., resulting in an exertion of a more effective activity of the present composition.

These compositions according to the present invention, prepared by mixing flavonoids in an amount of 0.0005–0.05-fold by weight of the processed Pfaffia products, exert more remarkable immunoenhancement and psychotropic activities among the later described activities. The compositions prepared by mixing flavonoids in an amount of 0.01–2-folds by weight of the processed Pfaffia products, d.s.b., exert an activity, specifically, an anti-allergic activity. The tonic activity of the present compositions is more augmented when the caffeine-containing plants are mixed with the processed Pfaffia products in an amount of 1–10-folds by weight of the processed Pfaffia products, d.s.b.

As described above, the compositions according to the present invention usually contain a flavonoid(s) and ecdysterone in an amount of 0.01–20 w/w % and 0.0001–2 w/w %, d.s.b., respectively. As for the compositions comprising the processed products of caffeine-containing plants, they generally contain 0.001–4 w/w % caffeine, d.s.b. The compositions can be processed into those in the form of liquids, powders, solids, semi-solids, pastes, or suspensions depending on the types and forms of the ingredients to be incorporated therein and on their processings, and of course all of them can be used arbitrarily.

The present compositions thus obtained exert strong immunoenhancement, anti-allergic, psychotropic, and tonic activities. Also the compositions exert conventional activities of Pfaffia incorporated therein, for example, strengthening activity, laxative activity, and activities for healing hemorrhoids, diarrhea, intestinal inflammation, skin injuries, and ulcers as described by Goro Hashimoto in "*Illustrated*

*Cyclopedia of Brazilian Medicinal Plants*", pp. 24–27, published by ABOC-SHA Ltd., Kanagawa, Japan (1996). Since the tastes such as bitterness and harshness inherent to Pfaffia are well improved, the present compositions can be arbitrarily used as orally administrable compositions that can maintain and promote the health and exert satisfactory therapeutic and preventive activities for diseases. These activities cooperatively function without inhibiting each other, and the present compositions have extremely-low toxicity. Therefore, the compositions can be advantageously used as tonics for enhancing physical and/or mental activities. As described later, in the case of containing nutritions such as saccharides, the compositions are extremely useful as nutritives and tonics. With these satisfactory activities, the present compositions can be arbitrarily used as immunoenhancers for treating and preventing diseases, antiallergics, psychotropics, and/or tonics.

The wording immunoenhancement activity as referred to in the present invention means one or more activities for growth promotion, extension, differentiation, and activation of immunocompetent cells of warm-blooded animals and humans; the following one or more activities can be mentioned: (1) enhancement of growth and/or extension of phagocytes such as macrophages, enhancement of cell differentiation of stem cells to the immunocompetent cells, digestion enhancement for external substances by phagocytosis of the immunocompetent cells, (2) enhancement of natural killer cells' lethal effect on tumor cells and virus-infected cells, (3) enhancement of B-cells' growth, enhancement of cell differentiation of stem cells to the B-cells, and enhancement of antibody producibility by the B-cells, (4) growth enhancement of cytotoxic T-cells, enhancement of cell differentiation of stem cells to the T-cells, and enhancement of T-cells' lethal effect on tumor cells and virus-infected cells, and (5) enhancement of growth of helper T-cells, enhancement of cell differentiation of stem cells to the T-cells, or enhancement of immune systems by enhancing the production of cytokines.

The wording anti-allergic activity as referred to in the present invention means one or more inhibitory activities for allergies, types I to IV, i.e., one or more of the following functions; (1) inhibitory effect on allergy, type I, through inhibition of IgE antibody production, inhibition of binding of the antibody to IgE receptors, and inhibition of biological reactions such as histamine release successively induced by the binding, (2) inhibitory effect on allergy, type II, through inhibition of target cell lysis by phagocytes and killer cells, (3) inhibitory effect on allergy, type III, through inhibition of biding of immuno-complexes formed in living bodies to complements, and inhibition of activation of complement systems such as anaphylatoxin induced successively by the binding, (4) inhibitory effect on allergy, type IV, through inhibition of sensitization by T-cell antigens, and inhibition of inflammatory cytokine production by the sensitized T-cells. Among these anti-allergic activities, the present compositions exert remarkable inhibitory-effect on allergy, type I.

The wording psychotropic activity as referred to in the present invention means one or more activities of improving and treating psychoneurosis instability and psychoneurosis. For example, the present compositions relieve anxiety and tension or exert ataractic activity, and improve depressive feeling or exert antidepressant- and/or psychoanaleptic-activities. Particularly, the compositions are effective for improving or inhibiting the symptom of anthropophobia such as erythrophobia.

The wording tonic activity as referred to in the present invention means activity of improving reproductive potential of either or both sexes of warm-blooded animals and humans. For example, the present compositions improve apareunia, sperm potential, and sperm formation activity, and promote or induce estrus of either or both sexes, resulting in desired effect.

As described foregoing, the present compositions enhance immune systems, inhibit allergic reactions, stabilize psychological conditions, and/or enhance sexual power to strength the bodies; and exert satisfactory effect in the treatment and/or prevention of menopausal syndrome and diseases or susceptive diseases induced by invasion of external substances such as bacteria, viruses, and fungi, by internal formation of tumor cells and virus-infected cells, and by allergic reactions such as nasal inflammation, anaphylaxis, pollenosis, alimentary allergy, atopic dermatitis, asthma, autoimmune hemolytic anemia, Goodpasture's syndrome, serum sickness, hypersensitivity pneumonitis, contact dermatitis, rheumatism, and ulcerative colitis; those such as psychologic and nervous diseases such as mental instability, anthropophobia, erythrophobia; and those accompanied by reduction of reproductive potential such as apareunia.

The present compositions include those in the form of orally administrable products in general; candy, troche, jelly, gummy, chewing gum, chocolate, juice, soft drink, alcohol, lactic acid beverage, sports drink or beverage, jam, cream, cookie, biscuit, senbei (a Japanese cracker), udon (a wheat vermicelli), soba (a buckwheat vermicelli), sausage, ham, kamaboko (a boiled fish paste), chikuwa (a kind of fish paste), hanpen (a cake of pounded fish), tsukudani (a food boiled down in soy), instant juice, and instant soup.

In addition to these products, the present compositions include other types of compositions which contain one or more of physiologically-acceptable carriers, excipients, diluents, adjuvants, stabilizers, and optionally at least one of other biologically active substances. Examples of such stabilizers are proteins including as serum albumin and gelatin; saccharides including glucose, sucrose, lactose, maltose, and trehalose, sugar alcohols such as sorbitol, maltitol, mannitol, and lactitol; and buffers comprising salts of citric acid or phosphoric acid mainly. Examples of the other biologically active substances are cyclosporin, FK506, cyclophosphamide, nitrogen mustard, triethylenethiophosphoramide, busulfan, pheramine mustard, chlorambucil, azathioprine, 6-mercaptopurine, 6-thioguanine, 6-azaguanine, 8-azaguanine, fluorouracil, cytarabine, methotrexate, aminopterin, mitomycin C, hydrochloric acid daunorubicin, actinomycin D, chromomycin A3, hydrochloric acid bleomycin, hydrochloric acid doxorubicin, cyclosporin A, L-asparaginase, vincristine, vinblastine, hydroxyurea, hydrochloric acid procarbazine, corticosteroid, lumin (1-1'-1"-trihepthyl-11-chinolyl(4)·4·4'-penthamethinchynocyanin-1, 1"diiodide), vitamins A, B, C, D, E, and K, amino acid, radio gold colloidal, potassium bromide, calcium lactate, calcium glycerophosphate, potassium iodide, reduced iron, sodium salt of heparin, chloral hydrate, meprobamate, oxazolam, phenytoin, elsinan, nicotinamide, chlorella extract, aloe extract, propolis extract, turtle extract, oyster extract, ginseng extract, lactic acid bacterium, yeast, royal jelly, and optionally interferon, TNF-α, erythropoietin, interleukin, cytokine receptor, and its antagonists.

The present compositions include medicaments in dosage unit form meaning that those containing processed Pfaffia products and flavonoids in an amount of, for example, one to several folds of a dose by integers up to fourfold or in an amount of measures of a dose down to 1/40, and have physically integrated forms for ease of administration.

Examples of such medicaments are injections, liquids, powders, granules, tablets, capsules, sublinguals, ophthalmic solutions, nebulae, suppositories, external medicines, etc. The present compositions are orally or parenterally administrable to patients and exert satisfactory therapeutic and preventive effect on susceptive diseases independently of their administration routes. Depending on the types and symptoms of susceptive diseases and on the ingredients of the compositions for immunopathies, the compositions can be administered to patients orally or parenterally such as intradermally, subcutaneously, intramuscularly, or intravenously, in a dose of about 0.1 mg to about 10 g/shot/adult, and preferably about one mg to about one g/shot/adult of processed Pfaffia products and flavonoids, d.s.b., 1–4 shots/day or 1–5 shots/week for one day to one year.

The following Experiments 1 to 5 describe the embodiments of the function, taste, and toxicity of the compositions according to the present invention:

Experiment 1

Preparation of processed products
Experiment 1-1
Pfaffia extract

Three kilograms of dried tuberous root chips of *Pfaffia glomerata* from Brazil and 45 l of deionized water were placed in a 100-l stainless steel mug, and the mixture was placed on a fire, and then allowed to stand for 40 min under boiling conditions. The resulting mixture was placed in a crate for filtration to obtain a 28.8 kg filtrate. The residue was collected in the same mug and mixed with 20 l deionized water, and the mixture was placed on a fire, and then allowed to stand for 30 min under boiling conditions. The resulting mixture was placed in a crate to obtain a 19.6 kg filtrate which was then pooled with the above filtrate. The pooled solution was treated with a basket-type centrifuge commercialized by Hitachi Tekkosho Co., Ltd., Tokyo, Japan, to remove insoluble substances, and concentrated using "HOROCEP HR5155F1", a reverse-osmosis membrane commercialized by Toyobo Co., Ltd., Tokyo, Japan, at a permeation rate of about 30 l/hour, into a 10.7 kg concentrate. The concentrate thus obtained was incubated for further concentration in a jacketed stainless-steel-tank at 80° C. for 21.5 hours to obtain a 2,770 g liquid Pfaffia extract as a processed Pfaffia product. The Pfaffia extract had a concentration of about 50 w/w %, d.s.b.

A portion of the Pfaffia extract was treated with the purification method for ecdysterone as disclosed by N. NISHIMOTO et al., in *Phytochemistry*, Vol. 32, pp. 1,527–1,530 (1993) to obtain a needle-like crystal. Conventional analysis of the crystal revealed that it had a melting point of 240–242° C. and a rotatory power of +89° ($=[\alpha]_D +89°$). Based on the fact that these data were well agreed with the physicochemical properties of ecdysterone as disclosed by N. NISHIMOTO et al., in *Phytochemistry*, Vol. 26, page 2,505 (1987), the present inventors identified the crystal with ecdysterone.

One milligram of the crystal was dissolved in a mixture of acetonitrile and water (=15:85 by volume) to give a total volume of two milliliters, and the solution was membrane filtered using a membrane filter with a pore size of 0.45 $\mu$m. The filtrate was diluted with the same solvent into 500 $\mu$g/ml, 200 $\mu$g/ml, 100 $\mu$g/ml, and 50 $\mu$g/ml ecdysterone solutions for standard solutions. Twenty $\mu$l aliquots of each standard solutions were analyzed on HPLC as indicated below. The conditions and apparatuses used were: "CAPCELL PAK $C_{18}$ AG120", a column commercialized by Shiseido Co., Ltd., Tokyo, Japan; a mixture solution of acetonitrile and water (=15:85 by volume) as an eluant; and a column temperature of 35° C.; and a flow rate of 0.5 ml/min. Using a visible-ultraviolet spectrophotometer "MODEL 875-UV" commercialized by Nippon Bunko Kogyo Co., Ltd., Tokyo, Japan, the sample solutions were monitored for absorbance at a wavelength of 240 nm. The data was treated with "CR-4A", a data processor commercialized by Shimadzu Techno-Research, Inc., Kyoto, Japan. As a result, all the standard solutions gave a main peak at a position corresponding to an elution time of about 17 min. The peak was for ecdysterone. Based on each peak area, a standard curve was drawn.

One gram of a Pfaffia extract obtained by the above method was weighed, mixed with a mixture solution of acetonitrile and water (=15:85 by volume) to give a total volume of 25 ml, followed by filtering the solution with a membrane having a pore size of 0.45 $\mu$m to obtain a filtrate. Similarly as in the case of the purified ecdysterone specimen, 20 $\mu$l of the filtrate was analyzed on HPLC to detect a peak with a retention time coincided with those of the peaks for the above standard solutions, followed by interpolating the peak area into the standard curve to confirm that the Pfaffia extract contained about one w/w % ecdysterone, d.s.b.

Experiment 1-2
Powdered guarana

"POWDERED GUARANA", a pulverized product of guarana commercialized by ONOBRAS Co., Ltd., São Paulo, Brazil, was used as a processed guarana product. Caffeine was detected in the guarana product on HPLC as shown in the below: One milligram per milliliter of anhydrous caffeine commercialized by Wako Pure Chemical Industries, Ltd., Tokyo, Japan, was prepared and diluted into 250 $\mu$g/ml, 100 $\mu$g/ml, 50 $\mu$g/ml, 25 $\mu$g/ml, and 10 $\mu$g/ml standard solutions. Twenty $\mu$l aliquots of the standard solutions were subjected to HPLC using "TSK GEL ODS-80$T_M$", a column having 4.6 mm in diameter and 15 cm in length, commercialized by Tosoh Corporation, Tokyo, Japan, and a mixture solution of methanol and 50 mM phosphate buffer (pH 6.5) containing 5 mM sodium octane sulfonate (1:4 by volume). The flow rate was 1.0 ml/min and a column temperature was 40° C. The eluates were monitored for absorbance at 270 nm using a visible-ultraviolet spectrophotometer "MODEL 875-UV" commercialized by Nippon Bunko Kogyo Co., Ltd., Tokyo, Japan. The data was treated with "CR-4A", a data processor commercialized by Shimadzu Techno-Research, Inc., Kyoto, Japan. As a result, all the standard solutions gave a main peak at a position corresponding to an elution time of about seven min. The peak was for caffeine. Based on each peak area, a standard curve was drawn. In parallel, 75 mg of the above POWDERED GUARANA was placed in a test tube and mixed with about 10 ml distilled water, and the mixture solution was boiled for 15 min, cooled, and admixed with distilled water to give a total volume of 25 ml. The solution was centrifuged at 10,000 rpm for five minutes, and the supernatant was collected, filtered using a membrane filter having a pore size of 0.45 $\mu$m. Similarly as in the case of the standard solutions, 20 $\mu$l of the filtrate was analyzed on HPLC to detect a peak with a retention time coincided with those of the peaks for the above standard solutions, followed by interpolating the peak area into the standard curve to confirm that the POWDERED GUARANA contained about four w/w % caffeine, d.s.b.

Experiment 1-3

Indigo extract

Aerial parts including leaves and stems of a fresh indigo plant were reaped in an about 10 kg by wet weight. After being removed concomitants such as dead leaves and weeds, the aerial parts were washed with running water, dehydrated, treated with "MODEL OMC-12", a chopper commercialized by Daido Sangyo Co., Ltd., Tokyo, Japan, to obtain an about 10 kg pulverized indigo. Three hundred and seventy grams of the pulverized product was mixed with 555 g deionized water, and the mixture was treated with "TRIOBLENDER", a blender commercialized by Torio Science Co., Ltd., Tokyo, Japan, for two minutes. The resulting mixture was centrifugally filtered, and 688 g of a supernatant was collected and placed in a stainless-steel mug, autoclaved at 121° C. for 10 min, cooled, and centrifuged at 4° C. and 15,000 rpm for 20 min, followed by collecting 619 g of a supernatant. The supernatant had a solid concentration of about 1.9%. To the supernatant was added deionized water to obtain an about one percent of indigo extract, d.s.b.

Experiment 2

Immunoenhancement action

A Pfaffia extract obtained by the method in Experiment 1-1, "αG HESPERIDIN PA", as a flavonoid, an enzyme-treated rutin commercialized by Toyo Sugar Refining Co., Ltd., Tokyo, Japan, and "αG RUTIN PS", an enzyme-treated rutin, Toyo Sugar Refining Co., Ltd., Tokyo, Japan, were mixed in appropriate amounts, and the mixture was diluted with refined water, sterilized using a membrane filter to obtain five types of specimens, sample Nos. 1–5 as shown in Table 1.

TABLE 1

| Composition* | Sample No. | | | | |
| --- | --- | --- | --- | --- | --- |
| | 1 | 2 | 3 | 4 | 5 |
| Pf | 50 mg/g | — | — | 50 mg/g | 50 mg/g |
| HG | — | 0.5 mg/g | — | 0.5 mg/g | — |
| RG | — | — | 0.5 mg/g | — | 0.5 mg/g |

Note: In Table numerals mean the solid weight of compositions per one gram of each sample.
*: The symbols "Pf", "HG", and "RG" mean Pfaffia extract, enzyme-treated hesperidin, and enzyme-treated rutin, respectively.

The five samples were examined for immunoenhancement activity as indicated in the below: Macrophages were collected from peritoneals of BALB/c mice, inoculated into 96-well microplates to adhere thereupon. To the microplates were added 0.1 ml/well of respective diluents prepared by diluting the five samples 100-folds with RPMI 1640 medium containing 10 v/v % fetal calf serum and 10 mM Hepes buffer (pH 7.4), followed by the incubation at 37° C. for five hours in a 5 v/v % $CO_2$ incubator. Each well was photographed, followed by calculating the percentage (%) of the number of extended macrophages to the number of total macrophages. As a control, a system was provided, where RPMI 1640 medium containing 10 v/v % fetal calf serum and 10 mM Hepes buffer (pH 7.4), was added to the microplates in place of the above diluents of the samples. The data is in Table 2.

TABLE 2

| Sample No. | 1 | 2 | 3 | 4 | 5 | Control |
| --- | --- | --- | --- | --- | --- | --- |
| Extended macrophage (%) | 12 | 10 | 9 | 21 | 20 | 5 |
| Remarks * | — | — | — | + | + | — |

Note*: The symbols "+" and "−" mean the present invention and example for reference, respectively.

In the data in Table 2, the balance between the values in the system with sample Nos. 1–5 and in the control system, when evaluated with respect to macrophage activating activity of the samples, shows that Pfaffia extract and flavonoids have a strong macrophage activating activity that is synergistically enhanced by combination use of Pfaffia extract and a flavonoid(s). This shows that the compositions of sample Nos. 4 and 5 as the present compositions exert a strong immunoenhancement activity. The enzyme-treated products of flavonoids used in this experiment are well known to be converted into free flavonoids by the action of glucosidase in vivo. These data indicate that intact flavonoids, which are not identical to their enzyme-treated products, can also be used in the present invention.

A Pfaffia extract obtained by the method in Experiment 1-1, the pulverized guarana in Experiment 1-2, an indigo extract obtained by the method in Experiment 1-3, "αG HESPERIDIN PA", an enzyme-treated hesperidin commercialized by Toyo Sugar Refining Co., Ltd., Tokyo, Japan, and "αG RUTIN PS", an enzyme-treated rutin, Toyo Sugar Refining Co., Ltd., Tokyo, Japan, were mixed in appropriate amounts, diluted with refined water, and sterilized by filtering to obtain 10 types of specimens, sample Nos. 6–15 in Table 3.

TABLE 3

| Composition* | Sample No. | | | | | | | | | |
| --- | --- | --- | --- | --- | --- | --- | --- | --- | --- | --- |
| | 6 | 7 | 8 | 9 | 10 | 11 | 12 | 13 | 14 | 15 |
| Pf | — | — | 50 mg/g | 50 mg/g | 50 mg/g | 50 mg/g | 50 mg/g | 50 mg/g | 50 mg/g | 50 mg/g |
| HG | — | — | 0.5 mg/g | — | 0.5 mg/g | 0.5 mg/g | 0.5 mg/g | — | — | — |
| RG | — | — | — | 0.5 mg/g | — | — | — | 0.5 mg/g | 0.5 mg/g | 0.5 mg/g |
| Gr | 50 mg/g | — | — | — | 50 mg/g | — | 50 mg/g | 50 mg/g | — | 50 mg/g |
| Id | — | 50 μg/g | — | — | — | 50 μg/g | 50 μg/g | — | 50 μg/g | 50 μg/g |

Note:
In Table numerals mean the solid weight of compositions per one gram of each sample.
*The symbols "Pf", "HG", "RG", "RG", "Gr", and "Id" mean Pfaffia extract, enzyme-treated hesperidin, enzyme-treated rutin, guarana extract, and indigo extract, respectively.

Similarly as the same method as above, these 10 samples were examined for immunoenhancement action, then evaluated based on the difference between the samples and control similarly as above. The data is in Table 4.

TABLE 4

| Sample No. | 6 | 7 | 8 | 9 | 10 | 11 | 12 | 13 | 14 | 15 | Control |
|---|---|---|---|---|---|---|---|---|---|---|---|
| Extended macrophage (%) | 8 | 7 | 20 | 19 | 25 | 24 | 28 | 24 | 24 | 27 | 6 |
| Remarks* | − | − | + | + | + | + | + | + | + | + | − |

Note:
*The symbols "+" and "−" mean the present invention and example for reference, respectively.

Addition of indigo extract and/or pulverized guarana to the sample Nos. 4 and 5 resulted in a synergistic macrophage activating activity, and this indicates that these compositions according to the present invention exert a strong immunoenhancement activity.

In place of the Pfaffia extract as used in Experiment 2, either of extracts of a bad-smelling perennial plant of the family Saururaceae, ginkgo, and chlorella, which were prepared in usual manner, was examined similarly as above. These extracts, which are folk medicines conventionally used in various places, showed no enhancement of macrophage activating action inherent to flavonoids, pulverized guarana, and indigo. The data shows that the present compositions, which are mixtures of folk medicines and natural substances, do exert extremely-high effect.

Experiment 3

Antiallerqic action

A Pfaffia extract obtained by the method in Experiment 1-1; "αG HESPERIDIN PA", as a flavonoid, an enzyme-treated hesperidin commercialized by Toyo Sugar Refining Co., Ltd., Tokyo, Japan; a pulverized guarana in Experiment 1-2; and a Japanese indigo extract obtained by the method in Experiment 1-3 were mixed, and the mixture was diluted with refined water, and sterilized by membrane filtration to obtain eight types of specimens, sample Nos. 16–23 in Table 5.

The eight samples were examined for antiallergic action by comparing their influence on passive cutaneous anaphylaxis in experimental animals. As described by Hideomi FUKUDA et al., in Zoku-Iyakuhin-no-Kaihatsu (Development of Pharmaceuticals, second series), titled "Animal Models for Diseases", Vol. 2, pp. 95–96 (1993), passive cutaneous anaphylaxis is known as a technique used for screening antiallergic agents, so that it can be useful for studying antiallergic activity of test samples.

Thirty wister male rats, 6-week-old, purchased from Charles River Japan, Inc., Tokyo, Japan, were first bred for one week in usual manner, then depilated on their dorsum parts and sensitized by injecting into three intradermal sites in each depilated part with 0.1 ml aliquots of an anti-2,4-dinitrophenylated ascaris extract serum (abbreviated as "antiDNP-AS", hereinafter), produced by LSL Ltd., Tokyo, Japan. After 47 hours from the sensitization, any one of the eight samples was orally administered to rats at a dose of one gram/head. As a control, there provided a system where sterilized refined water was orally administered to rats in place of the samples. The same specimen of each sample was administered in triplicate to three rats in the same protocol. After 48 hours from the sensitization, the rats were administered through their tail veins with one milliliter of physiological saline containing a 0.5 mg/ml 2,4-dinitrophenylated ascaris extract (abbreviated as "DNP-AS"), produced by LSL Ltd., Tokyo, Japan, and 0.5 w/v % Evans blue to induce passive cutaneous anaphylaxis. After 30 min from the administration of DNP-AS, the rats were let blood to death, followed by exfoliating their dorsum skins, cutting pigment maculas in a prescribed size, and measuring the amount of exuded pigments from blue-stained parts in accordance with the method by S. KATAYAMA et al., in Microbiology Immunology, Vol. 22, pp. 89–101 (1978); Add one milliliter of 1.2-N potassium hydroxide to each skin debris, incubate the mixture at 37° C. for over 15 hours to lyse skin tissues, and add to the resulting mixture nine milliliters of a mixture of 0.6-N phosphate and acetone (=5:13 by volume) to extract pigments. The extract was centrifuged in usual manner, followed by measuring the absorbance of the resulting supernatant at a wavelength of 620 nm and calculating the amount of exuded pigments based on the measurement. The mean value of the amounts of exuded pigments for each administered sample is in Table 6.

TABLE 5

| Composition* | Sample No. | | | | | | | |
|---|---|---|---|---|---|---|---|---|
| | 16 | 17 | 18 | 19 | 20 | 21 | 22 | 23 |
| Pf | 100 mg/g | — | — | — | 100 mg/g | 100 mg/g | 100 mg/g | 100 mg/g |
| HG | — | 10 mg/g | — | — | 10 mg/g | 10 mg/g | 10 mg/g | 10 mg/g |
| Gr | — | — | 50 mg/g | — | — | 50 mg/g | — | 50 mg/g |
| Id | — | — | — | 1 mg/g | — | — | 1 mg/g | 1 mg/g |

Note:
In Table numerals mean the solid weight of compositions per one gram of each sample.
*The symbols "Pf", "HG", "Gr", and "Id" mean Pfaffia extract, enzyme-treated hesperidin, guarana extract, and indigo extract, respectively.

TABLE 6

| Sample No. | 16 | 17 | 18 | 19 | 20 | 21 | 22 | 23 | Control |
|---|---|---|---|---|---|---|---|---|---|
| Amount of exuded pigments (μg/ml) | 4.3 | 3.3 | 4.8 | 4.9 | 2.3 | 2.0 | 2.0 | 1.8 | 5.0 |
| Remarks* | − | − | − | − | + | + | + | + | − |

Note:
*The symbols "+" and "−" mean the present invention and example for reference, respectively.

As shown in Table 6, the pigment exudation from the rats with passive cutaneous anaphylaxis was significantly inhibited by Pfaffia extract and flavonoids. The level of inhibition was synergistically enhanced by the combination use of Pfaffia extract and flavonoids, and was more enhanced by the addition of an indigo extract and/or pulverized guarana. The use of "αG RUTIN PS", an enzyme-treated rutin, Toyo Sugar Refining Co., Ltd., Tokyo, Japan, which was used as a flavonoid in this experiment in place of the enzyme-treated hesperidin, resulted in substantially the same result. Since the enzyme-treated products of flavonoids used in this experiment are well known to be converted into free flavonoids by the action of glucosidase in vivo, the above result shows that intact flavonoids as non-enzyme-treated products can also be used in this invention similarly as their enzyme-treated products. These results confirm that the present compositions have a strong antiallergic activity.

In place of the Pfaffia extract in Experiment 3, either of extracts of bad-smelling perennial plant of the family Saururaceae, ginkgo, and chlorella, which were prepared in usual manner, was used and experimented similarly as above. These extracts are folk medicines conventionally used in various places, but they showed no enhancement activity for antiallergic action inherent to flavonoids, pulverized guarana, and indigo extract. This result shows that the present compositions exert strong effect even though they are compositions made of folk medicines and natural products.

Experiment 4

Psychotropic action

A Pfaffia extract obtained by the method in Experiment 1-1; "αG HESPERIDIN PA", as a flavonoid, an enzyme-treated hesperidin commercialized by Toyo Sugar Refining Co., Ltd., Tokyo, Japan; a pulverized guarana in Experiment 1-2; and an indigo extract obtained by the method in Experiment 1-3 were mixed in appropriate amounts, and the mixture was diluted with refined water, and sterilized by membrane filtration to obtain eight types of specimens, sample Nos. 24–31 in Table 7.

These samples were examined for psychotropic action in accordance with the method using the rotarod test reported by Shigeru MORIMOTO et al., in Nichi-Yakuri-Shi (Folia Pharmacol. Jpn.), Vol. 104, pp. 39–49 (1994); Sprague-Dawley male rats, 5-week-old, were allowed to ride on a wooden rod, which had a diameter of 1.2 cm and was rotating at a rate of six revolutions per minute, at five to six times per rat. Thereafter, the time until the rats were fallen down from the rod after the stopping of the rotation (hereinafter called "reaction time" in Experiment 3) was measured, and rats giving substantially a constant reaction time for two to three trials were selected and orally administered with the above samples. The dose was one gram per rat, and as a control there provided a system where rats were similarly administered with sterilized distilled water. The same sample was administered to three rats in the same protocol. After one hour from the administration, the reaction time for each rat was measured, then the mean value for each sample was calculated. Presupposing that the reaction time before the administration of each sample was one, the reaction time after the administration of each sample was relatively expressed and compared with that of control. The relative mean values of the samples administered to rats are in Table 8.

TABLE 8

| Sample No. | 24 | 25 | 26 | 27 | 28 | 29 | 30 | 31 | Control |
|---|---|---|---|---|---|---|---|---|---|
| Reaction time (relative value) | 1.7 | 1.6 | 1.3 | 1.1 | 2.3 | 2.4 | 2.4 | 2.7 | 1.3 |
| Remarks* | − | − | − | − | + | + | + | + | − |

Note:
*The symbols "+" and "−" mean the present invention and example for reference, respectively.

As shown in Table 8, the reaction time of rats was more markedly prolonged by Pfaffia extract and flavonoids than in control. The level of the prolonged reaction time to the control was significantly increased by the combination use of Pfaffia extract and flavonoids, and was more increased by further addition of an indigo extract and/or pulverized guarana. The use of "αG RUTIN PS", an enzyme-treated rutin, Toyo Sugar Refining Co., Ltd., Tokyo, Japan, which was used in this experiment as a flavonoid in place of the enzyme-treated hesperidin, resulted in substantially the same result. Since the enzyme-treated products of flavonoids used in this experiment are well known to be converted into free flavonoids by the action of glucosidase in vivo, the above result shows that intact flavonoids as non-enzyme-treated products can also be used in this invention similarly as their enzyme-treated products. These results confirm that the present compositions have a strong psychotropic activity.

TABLE 7

| | Sample No. | | | | | | | |
|---|---|---|---|---|---|---|---|---|
| Composition* | 24 | 25 | 26 | 27 | 28 | 29 | 30 | 31 |
| Pf | 50 mg/g | — | — | — | 50 mg/g | 50 mg/g | 50 mg/g | 50 mg/g |
| HG | — | 0.5 mg/g | — | — | 0.5 mg/g | 0.5 mg/g | 0.50 mg/g | 0.5 mg/g |
| Gr | — | — | 50 mg/g | — | — | 50 mg/g | — | 50 mg/g |
| Id | — | — | — | 50 μg/g | — | — | 50 μg/g | 50 μg/g |

Note:
In Table numerals mean the solid weight of compositions per one gram of each sample.
*The symbols "Pf", "HG", "Gr", and "Id" mean Pfaffia extract, enzyme-treated hesperidin, guarana extract, and indigo extract, respectively.

Experiment 5

Tonic action

By comparing sperm-forming ability in experimental mice, the eight specimens of sample Nos. 16–23, prepared in Experiment 3 and shown their compositions in Table 5, were examined for tonic action. ICR male mice, 18-week-old, were orally administered with 0.5 g/shot/mouse of any one of the specimens. The administration was scheduled five shots a week and continued over three weeks, resulting in 15 shots/mouse in total. As a control, there provided a system where sterilized distilled water was similarly administered to rats. The same specimen of each sample was respectively administered to three rats. On the next day after the final administration, 0.5 ml/mouse of a labelled bromodeoxyuridine reagent enclosed in the cell growth detection kit commercialized by Amersham Corp., Div., Amersham International, Arlington Heights, USA, was intraperitoneally administered to the mice. After two hours from the administration, the rats' testicles were extracted and soaked in a 10% buffered formalin solution for two days. After the soaking, the testicles were prepared into paraffine embedded fragments, followed by detecting and measuring the intracellular intake of bromodeoxyuridine for counting the number of proliferated cells, i.e., sperm formation ability of each sample, by immunohistochemistry staining using an anti-bromodeoxyuridine monoclonal antibody, according to the protocol affixed to a cell-growth-detection kit commercialized by Amersham Corp., Div., Amersham International, Arlington Heights, USA. Stained cells among the proliferated cells, which were macroscopically observed within a view of a microscope at 100 magnifications, were counted to determine the mean value of stained cells with respect to each sample and to express the value with a relative value when the value of control was regarded as one. The results are in Table 9.

TABLE 9

| Sample No. | 16 | 17 | 18 | 19 | 20 | 21 | 22 | 23 | Control |
|---|---|---|---|---|---|---|---|---|---|
| Reaction time (relative value) | 1.7 | 1.2 | 1.6 | 1.1 | 2.2 | 3.0 | 2.4 | 3.3 | 1 |
| Remarks * | – | – | – | – | + | + | + | + | – |

Note:
*The symbols "+" and "–" mean the present invention and example for reference, respectively.

As shown in Table 9, the number of stained cells was remarkably increased by the administration of Pfaffia extract and flavonoids, and the increase was synergistically increased when the extract and flavonoids were used in combination. The synergistic increment was more critically enhanced by the addition of indigo extracts and/or pulverized extracts. In place of the enzyme-treated hesperidin used as a flavonoid in this experiment, the use of "αG RUTIN PS", an enzyme-treated rutin, Toyo Sugar Refining Co., Ltd., resulted in substantially the same result. The enzyme-treated product of a flavonoid used in this experiment is well known to be converted into free flavonoid by glucosidase in vivo; the result shows that flavonoids, non-enzyme-treated products, can also be used in the present invention. These results show that the present compositions have a strong tonic activity.

Experiment 6

Taste of composition

A Pfaffia extract obtained by the method in Experiment 1-1; "αG HESPERIDIN PA", as a flavonoid, an enzyme-treated hesperidin commercialized by Toyo Sugar Refining Co., Ltd., Tokyo, Japan; "αG RUTIN PS", an enzyme-treated rutin, Toyo Sugar Refining Co., Ltd., Tokyo, Japan; and sucrose were mixed in appropriate amounts, and the mixture was diluted with refined water, and sterilized by membrane filtration to obtain seven types of specimens, sample Nos. 32–38 in Table 10.

TABLE 10

| | Sample No. | | | | | | |
|---|---|---|---|---|---|---|---|
| Composition | 32 | 33 | 34 | 35 | 36 | 37 | 38 |
| Pf | 50 mg/g | — | — | — | 50 mg/g | 50 mg/g | 50 mg/g |
| HG | — | 0.5 mg/g | — | — | 0.5 mg/g | — | — |
| RG | — | — | 0.5 mg/g | — | — | 0.5 mg/g | — |
| Sc | — | — | — | 0.5 mg/g | — | — | 0.5 mg/g |

Note:
In Table numerals mean the solid weight of compositions per one gram of each sample.
*The symbols "Pf", "HG", "RG", and "Sc" mean Pfaffia extract, enzyme-treated hesperidin, enzyme-treated rutin, and sucrose, respectively.

The seven samples were evaluated by a panel test on taste; The samples were allowed to stand in a room kept at 24° C., and an about spoonful of each of which was allowed to be drunken by a panel consisting of ten males and six females. Thereafter, the panel were asked to evaluate the samples' taste based on the three grades of; (A) orally taken freely, (B) orally taken nearly freely but having bitterness and harshness, and (C) orally taken unwillingly due to its stronger bitterness and harshness. For each sample, the numbers of panel in each evaluation were summed up. The results are in Table 11.

TABLE 11

| Sample No. | 32 | 33 | 34 | 35 | 36 | 37 | 38 |
|---|---|---|---|---|---|---|---|
| Grade A | 0 | 14 | 13 | 16 | 14 | 15 | 1 |
| Grade B | 0 | 2 | 3 | 0 | 2 | 1 | 4 |
| Grade C | 16 | 0 | 0 | 0 | 0 | 0 | 11 |
| Remarks* | – | – | – | – | + | + | – |

Note:
*The symbols "–" and "+" mean the present invention and example for reference, respectively.

As shown in Table 11, the taste of Pfaffia in itself is satisfactorily-highly improved by the incorporation of Pfaffia extract and flavonoids. Similarly as above, the panel test using the sample Nos. 36 and 37 in addition to the pulverized guarana and the indigo extract resulted in a conclusion that they can also be easily administered orally. The data shows that the bitterness and harshness inherent to Pfaffia according to the present compositions is effectively reduced by a large margin.

Experiment 7

Acute toxicity test

After freeze-dried, the specimens of sample Nos. 8–15 in Experiment 2 and the specimens of sample Nos. 20–23 in Experiment 3 were tested for acute toxicity by orally administering to dd-mice, 7-week-old and about 19–21 g by weight. No mouse died up to a dose of 0.5 g/mouse, and further dose test was impossible. These data show that the present compositions are satisfactorily-low in toxicity.

The followings are the preferred embodiments for describing the compositions according to the present invention in more detail:

EXAMPLE 1

Powdery composition

To 2,770 g of an about 50% liquid Pfaffia extract, d.s.b., obtained by the method in Experiment 1-1, was added 6,879 g of "TREHAOSE®", a trehalose product commercialized by Hayashibara Shoji, Inc., Ltd., Okayama, Japan, and the mixture was divided into five portions and treated 5-times with "5DM", a mixer commercialized by Dalton Co., Tokyo, Japan, retained at 60° C. for 17 hours in "DK83", a dryer commercialized by Yamato Co., Tokyo, Japan, and dried in vacuo at 60° C. for four and half hours by a vacuum dryer commercialized by Yamato Co., Tokyo, Japan. Using "POWER-MIL P3", a pulverizer commercialized by Dalton Co., Tokyo, Japan, to obtain a powder containing Pfaffia extract.

One hundred grams of "αG HESPERIDIN PA", an enzyme-treated hesperidin commercialized by Toyo Sugar Refining Co., Ltd., Tokyo, Japan, and 900 g "TREHAOSE®", a trehalose commercialized by Hayashibara Shoji, Inc., Ltd., Okayama, Japan, were mixed by "5DM", a mixer commercialized by Yamato Co., Tokyo, Japan, and pulverized by "POWER MIL P-3", a pulverizer commercialized by Yamato Co., Tokyo, Japan, to obtain a powder containing flavonoids.

To 619 g of a liquid indigo extract with a solid concentration of about 1.9%, obtained by the method in Experiment 1-3, was added 8,636 g of "TREHAOSE®", a trehalose product commercialized by Hayashibara Shoji, Inc., Okayama, Japan, followed by allowing the mixture to stand at ambient temperature for 15 hours and pulverized by "POWER MIL P-3", a pulverizer commercialized by Dalton Co., Tokyo, Japan, to obtain a 9,141 g powdery indigo extract.

Seven hundred grams of the above powdery Pfaffia extract, 100 g of a powdery flavonoid, 100 g of a powdery indigo extract, and 100 g of the pulverized guarana in Experiment 1-2 were mixed by "5DM", a mixer commercialized by Dalton Co., Tokyo, Japan, to obtain a composition according to the present invention. The analysis of the composition in accordance with the method in Experiments 1-1 and 1-3 confirmed that the composition contains about 0.05 w/w % ecdysterone and about 0.4 w/w % caffeine, d.s.b.

The product can be easily taken orally because the bitterness and harshness inherent to Pfaffia are satisfactorily lowered while retaining mild sweetness of trehalose. Because the product has a satisfactory immunoenhancement action, antiallergic action, psychotropic action, and tonic action, and because these actions function cooperatively without inhibiting one another, the product imparts physical and spiritual activities to living bodies. The product is nutritive because it contains trehalose, and it is extremely low in toxicity. The present composition with these satisfactory properties can be arbitrarily used in food and pharmaceutical industries in the maintenance and promotion of health, and in the treatment and prevention of and recovery from susceptive diseases such as immunopathies, psychoneurosis and/or sexual ability.

EXAMPLE 2

Tablet composition

A powdery composition obtained by the method in Example 1 and "LUMIN", a cell activator commercialized by Japanese Research Institute for Photosensitizing Dyes Co., Ltd., Okayama, Japan, were mixed, and the mixture was tabletted by a 20 R punch having a diameter of 12 mm to obtain a tablet, as the present composition, containing about 2% LUMIN, d.s.b. The product has a satisfactory immunoenhancement activity, antiallergic activity, psychotropic activity, and tonic activity, exerts cell activating activity, and imparts physical and spiritual activities when administered to living bodies. The product is nutritious because it contains trehalose, and it is extremely low in toxicity. The present composition having these satisfactory properties can be arbitrarily used in food and pharmaceutical industries in the maintenance and promotion of health, and in the treatment and prevention of and recovery from susceptive diseases such as immunopathies, psychoneurosis and/or sexual ability.

EXAMPLE 3

Milky composition

One kilogram of an about 50% liquid Pfaffia extract, d.s.b., obtained by the method in Experiment 1-1, and 50 g "αG RUTIN PA", an enzyme-treated rutin commercialized by Toyo Sugar Refining Co., Ltd., Tokyo, Japan, were mixed to homogeneity and freeze-dried. To 100 g of the freeze-dried product were added 250 g "TREHAOSE®", a trehalose product commercialized by Hayashibara Shoji, Inc., Okayama, Japan, 50 g polyoxyethylene behenyl ether, 100 g polyoxyethylene sorbitol tetraoleate, 50 g oil-soluble glycerol monostearate, 50 g behenyl alcohol, 100 g avocado oil, and adequate amounts of vitamin E and an antiseptic. The mixture was dissolved by heating in conventional manner, mixed with 500 g 1,3-butylene glycol, 10 g carboxyvinyl polymer, and 8.5 kg refined water, and emulsified by a homogenizer into a milky lotion as the present composition. When applied to skins and mucosas, the product exerts its immunoenhancement activity. Since the product has antiallergic activity, it can be applied to patients without causing side effects. In addition, the product can be arbitrarily used to treat/prevent skin carcinomas and used as a sun screening and skin whitening in cosmetic and pharmaceutical industries.

EXAMPLE 4

Hard candy

To 300 g "TREHASTER®", a starch syrup containing trehalose commercialized by Hayashibara Shoji, Inc., Okayama, Japan, was added 800 g of a hydrogenated malt syrup with a moisture content of 25 w/w % and dissolved by mixing. The solution was concentrated in vacuo up to give a moisture content of below 2 w/w %, and the concentrate was mixed with 10 g citric acid and adequate amounts of a lemon flavor and a color, and further mixed and kneaded with 10 g of a freeze-dried product obtained by the method in Example 3. The resulting mixture was shaped in usual manner into a hard candy according to the present invention. The product is a hard candy which has high-quality sweetness, adequate bitterness, less hygroscopicity and meltability, and satisfactory biting property. Because the product has strong immunoenhancement, antiallergic, psychotropic, and/or tonic activities that function cooperatively without inhibiting one another, it imparts physical and spiritual activities to living bodies when administered to them. Therefore, the product effectively nourishes and strengthens the bodies during the decline of biological functions due to overwork, chilling conditions, and undernourishment, and also promotes the therapeutic effects of other therapies.

EXAMPLE 5

Soft drink

One hundred grams of a powdery composition obtained by the method in Example 1, 50 g of an isomerized sugar, 0.5 g citric acid, and 0.5 g L-ascorbic acid were mixed with water into a soft drink containing the present composition weighing one kilogram in total. The product has mild sweetness, adequate bitterness, refreshing taste, and satisfactory flavor and taste. Because the product has strong immunoenhancement, antiallergic, psychotropic, and/or tonic activities that function cooperatively without inhibiting one another, it imparts physical and spiritual activities to living bodies when administered to them. Thus, the product effectively nourishes and strengthens the bodies during the decline of biological functions due to overwork, chilling conditions, and undernourishment, and promotes the therapeutic effects of other therapies.

EXAMPLE 6

Synthetic sake 6,518 g of a 30 v/v % aqueous alcohol solution, 600 g of a 70% aqueous glucose solution, 50 g "TETRUP®", a maltotetraose-containing syrup commercialized by Hayashibara Shoji, Inc., Okayama, Japan, 11.1 g succinic acid, 3.66 g of a 75% aqueous lactic acid solution, 2.3 g sodium glutamate, 1.2 g glycine, 1.2 g alanine, 2.22 g sodium succinate, 1.6 g sodium chloride, 1.4 g natural salt, 200 g of a powdery composition obtained by the method in Example 1, and 2,500 g water to obtain a raw sake. The raw sake was diluted with water into a 15–16 v/v % alcohol solution, a synthetic sake containing the present composition. The product is an alcohol beverage that has mild sweetness, adequate bitterness, and satisfactory flavor and taste. Because the product has strong immunoenhancement, antiallergic, psychotropic, and/or tonic activities that function cooperatively without inhibiting one another, it imparts physical and spiritual activities to living bodies when administered to them. Thus, the product effectively nourishes and strengthens the bodies during the decline of biological functions due to overwork, ageing, chilling conditions, and undernourishment, and promotes the therapeutic effects of other therapies.

EXAMPLE 7

Chewing gum

Two parts by weight of a powdery composition obtained by the method in Example 1, 6 parts by weight of glucose, 2 parts by weight of a gum base melted by heating to the extent being softened, and an adequate amount of a peppermint flavor, and the mixture was kneaded by a roll and shaped into a chewing gum containing the present composition. The product has mild sweetness, adequate bitterness, refreshing flavor and taste, and satisfactory texture. Because the product has strong immunoenhancement, antiallergic, psychotropic, and/or tonic activities that function cooperatively without inhibiting one another, it imparts physical and spiritual activities to living bodies when administered to them. Thus, the product effectively nourishes and strengthens the bodies during the decline of biological functions due to overwork, chilling conditions, and undernourishment, and promotes the therapeutic effects of other therapies.

EXAMPLE 8

Suppository

One kilogram of an about 50% liquid Pfaffia extract, obtained by the method in Experiment 1-1, and 5 g of "αG RUTIN PA", an enzyme-treated rutin commercialized by Toyo Sugar Refining Co., Ltd., Tokyo, Japan, were mixed to homogeneity and freeze-dried. To 100 g of the freeze-dried product were added 720 g polyethyleneglycol #1000 and 180 g of polyethyleneglycol #4000, and the mixture was in usual manner prepared into a suppository as the present composition. Because of its satisfactory immunoenhancement activity, the product exerts satisfactory effect in the treatment and prevention of and the promotion of recovery of health from carcinogenic diseases in and around the large intestines and rectums such as large bowel cancers and colon cancers when administered to patients.

As described above, the present invention was made based on a complete original finding that the compositions, which contain processed products of Pfaffia and flavonoids, exert strong immunoenhancement antiallergic, psychotropic, and/or tonic activities that are sufficiently effective in the maintenance and promotion of health and the treatment and prevention of diseases. When administered to living bodies, these activities function cooperatively without inhibiting one another to impart the bodies physical and/or spiritual activities. The compositions have reduced bitterness and harshness inherent to Pfaffia and are satisfactorily low in toxicity. Thus, the present compositions are extremely useful as orally-administrable strengthening agents. Other types of the present compositions containing nutritive sources such as saccharides are also extremely useful as nutritives and strengthening agents. The present compositions with these remarkable functions and activities are extremely useful as agents for treating and preventing susceptive diseases.

The present invention with these outstanding functions and activities is a significant invention that greatly contributes to this field.

We claim:

1. A composition which comprises a flavonoid and a processed product of a plant of the genus Pfaffia, said flavonoid being a member selected from the group consisting of hesperidin, rutin, naringin, eriodictin, hesperetin, quercetin, naringenin, eriodictyol, enzyme-treated hesperidin, enzyme-treated rutin, enzyme-treated naringin, and enzyme-treated eriodictin;

said processed product being obtained by physically and/or chemically treating said plant;

wherein the amount of said flavonoid is in an amount of 0.001–1-fold of said processed product, on a dry solid basis;

said composition providing immunoenhancement and antiallergic activities compound with each of said flavonoid and said processed product.

2. The composition of claim 1, wherein said processed product is a minced, disrupted, ground, pulverized, pressed, fermented and/or extracted root of said plant.

3. The composition of claim 1, wherein said processed product is obtained by extracting the root of said plant with water and/or an alcohol.

4. The composition of claim 1, wherein said processed product contains ecdysterone and/or its derivative.

5. The composition of claim 4, which contains 0.0001–2 w/w % of said ecdysterone and/or its derivative, on a dry solid basis.

6. The composition of claim 1, which contains 0.01–20 w/w % of said flavonoid, on a dry solid basis.

7. The composition of claim 1, which contains a processed product of a caffeine-containing plant and/or a processed product of indican-containing plant in addition to said processed product of said plant of the genus Pfaffia.

8. The composition of claim 7, wherein said processed product of said caffeine-containing plant is a minced, disrupted, ground, pulverized, pressed, fermented and/or extracted seed of said plant; and said processed product of said indican-containing plant is a minced, disrupted, ground, pulverized, pressed, fermented and/or extracted leaf and/or stem of said plant.

9. The composition of claim 8, wherein said extract of said caffeine-containing plant is obtained by extracting said seed with water and/or an alcohol, and said extract of said indican-containing plant is obtained by extracting said leaf and/or said stem with water and/or an alcohol.

10. The composition of claim 7, wherein said caffeine-containing plant is a plant of the genus Paullinia, Coffea, *Thea sinensis*, or Cola; and said indican-containing plant is a plant of the genus Percicaria or Indigofera.

11. The composition of claims 10, wherein said caffeine-containing plant is Guarana of the genus Paullinia, and said indican-containing plant is an indigo plant of the genus Percicaria.

12. The composition of claim 7, which contains said processed product of said caffeine-containing product in an amount of 0.01–10-folds of said processed product of said plant of the genus Pfaffia.

13. The composition of claim 7, which contains said processed product of said indican-containing product in an amount of 0.0001–0.1-fold of said processed product of said plant of the genus Pfaffia.

14. The composition of claim 7, which contains 0.0001–4 w/w % caffeine and/or its derivative, on a dry solid basis.

15. The composition of claim 1, which contains a saccharide.

16. The composition of claim 15, wherein said saccharide is one or more members selected from the group consisting of trehalose, anhydrous crystalline trehalose, maltose, and anhydrous crystalline maltose.

17. The composition of claim 1, which is in the form of a liquid, solid, powder, semi-solid, paste or suspension.

18. The composition of claim 1, which is for an orally administrable composition.

19. The composition of claim 1, which is for an antasthenic.

20. The composition of claim 1, which is for an agent for immunoenhancement, antiallergic, psychotropic, and/or tonic.

* * * * *